United States Patent [19]

Woo et al.

[11] 4,145,529
[45] Mar. 20, 1979

[54] PRODUCTION OF 3'-DEOXYBUTIROSINA A

[75] Inventors: Peter W. K. Woo; Theodore H. Haskell, both of Ann Arbor, Mich.

[73] Assignee: Parke, Davis & Company, Detroit, Mich.

[21] Appl. No.: 600,677

[22] Filed: Jul. 31, 1975

[51] Int. Cl.[2] .................. A61K 31/71; C07H 15/22
[52] U.S. Cl. .................... 536/17; 424/180; 536/10
[58] Field of Search ............. 260/210 AB, 210 K; 536/17

[56] References Cited

U.S. PATENT DOCUMENTS

| | | | |
|---|---|---|---|
| 3,826,802 | 7/1974 | Kawaguchi et al. | 260/210 AB |
| 3,886,138 | 5/1975 | Naito et al. | 260/210 AB |
| 3,920,628 | 11/1975 | Daniels | 260/210 AB |
| 3,932,382 | 1/1976 | Ohki et al. | 260/210 K |
| 3,960,833 | 6/1976 | Naito et al. | 536/17 |
| 4,065,615 | 12/1977 | Horii et al. | 536/17 |

Primary Examiner—Johnnie R. Brown
Attorney, Agent, or Firm—David B. Ehrlinger; Stephen Raines

[57] ABSTRACT

O-2,6-Diamino-2,3,6-trideoxy-α-D-ribo-hexopyranosyl-(1→4)-O-[β-D-xylofuranosyl-(1→5)]-N$^1$-[(S)-4-amino-2-hydroxy-1-oxobutyl]-2-deoxystreptamine, also known as 3'-deoxybutirosin A and acid addition salts of said compound. These compounds exhibit a wide spectrum of antibacterial activity.

The above compounds are produced by the reduction of a tetra-N-protected-3'-arylthio-3'-deoxybutirosin A compound having the formula:

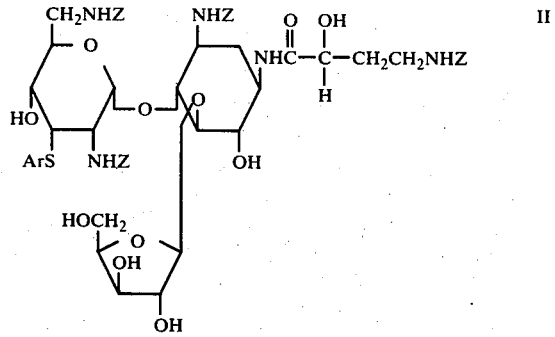

2 Claims, No Drawings

PRODUCTION OF 3'-DEOXYBUTIROSIN A

SUMMARY AND DETAILED DESCRIPTION

The present invention relates to new chemical compounds and to methods for their production. More specifically, this invention relates to O-2,6-diamino-2,3,6-trideoxy-α-D-ribo-hexopyranosyl-(1→4)-O-[β-D-xylofuranosyl-(1→5)]-N$^1$-[(S)-4-amino-2-hydroxy-1-oxobutyl]-2-deoxystreptamine, also known as 3'-deoxybutirosin A, and to acid addition salts thereof. 3'-Deoxybutirosin A may be represented by the formula:

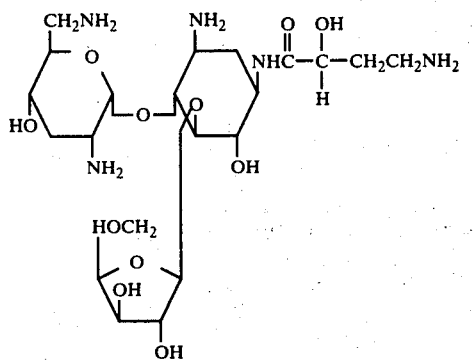

In addition, this invention relates to methods for the preparation of 3'-deoxybutirosin A (I) and salts thereof from an N-protected arylthio-deoxybutirosin A compound.

More specifically, the invention relates to the preparation of 3'-deoxybutirosin A (I) by the reduction of a tetra-N-protected-3'-arylthio-3'-deoxybutirosin A compound having the formula:

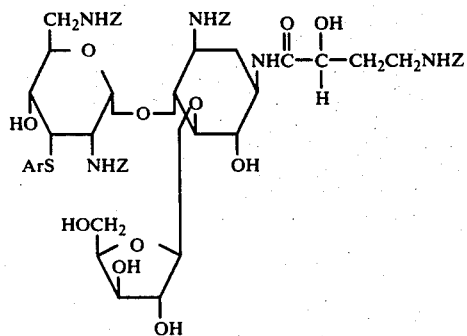

wherein Z is a protective group which is readily removed by reduction, preferably a group of the formula

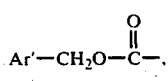

wherein Ar' is an aryl group such as

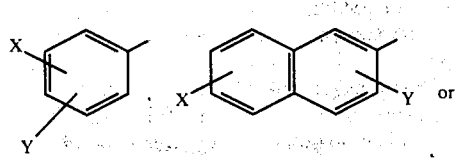

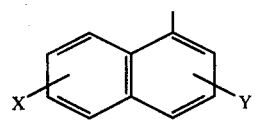

wherein X or Y is hydrogen, halogen, nitro, lower alkyl of from one to four carbon atoms, lower alkoxy of from one to four carbon atoms, etc., the most preferred group represented by

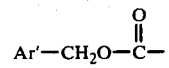

is carbobenzoxy, and Ar is a group such that the group ArS is readily removed by reduction, preferably Ar is an aryl group of the formula:

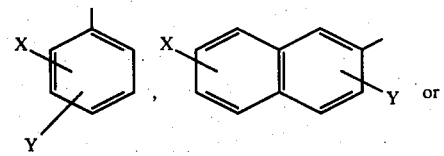

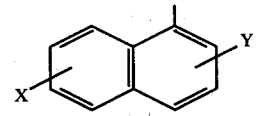

wherein X or Y is hydrogen, halogen, nitro, lower akyl of from one to four carbon atoms, lower alkoxy of from one to four carbon atoms, etc. The ArS group of first choice is phenylthio.

The reduction may be achieved either catalytically or chemically.

The catalytic reduction is carried out using hydrogen in the presence of a noble metal catalyst, such as platinum, palladium, etc., optionally supported on a carrier such as charcoal or barium sulfate, the preferred catalyst being palladium oxide on barium sulfate which is transformed by hydrogen to palladium metal on barium sulfate.

The hydrogen pressure that the reaction is conducted under is not critical and generally pressures of from about one to about three atmospheres are employed.

Most standard solvents used in catalytic hydrogen reactions may be employed, although water miscible, nonreactive solvents are preferred. These include lower alkanols of from one to three carbon atoms, lower alkanoic acids of from one to three carbon atoms, tetrahydrofuran, dioxane and mixtures of these. A preferred solvent is a methanol-acetic acid mixture. The presence of an acid in the reaction mixture is desirable so that the progress of the reaction can be measured by carbon dioxide evolution, indicating reductive cleavage of the N-[(arylmethoxy)carbonyl] groups.

While the temperatures and times are not critical, the reaction is generally conducted at about room temperature (20°–30° C.) until, under acid conditions, there is no further carbon dioxide evolution and the removal of the arylthio group is complete, as indicated by thin layer chromatography (about 10 to 60 hours).

While at a minimum, sufficient hydrogen is needed to completely reductively cleave the N-(arylmethoxy)carbonyl groups and the arylthio group, a large quantity of catalyst is required, generally from 300 percent to 700 percent based on the weight of compound II.

The compound of the invention having structure I may be isolated as the free base or converted to an acid-addition salt by reaction with any of various inorganic and organic acids such as hydrochloric acid, sulfuric acid, phosphoric acid, pamoic acid, carbonic acid, etc., and isolated as such.

Another method for the conversion of a tetra-N-protected-3'-arylthio-3'-deoxybutirosin A (II) into compound I utilizes a sodium in liquid ammonia reaction.

This reaction is generally carried out at the boiling point (−33° C.) of the solvent liquid ammonia; however, lower temperatures may be employed, such as carrying out the reaction in a dry ice-acetone bath (approximately −60° C.).

Sodium is added until a transparent blue color appears which lasts for from thirty seconds to about one minute.

The free base product may be isolated, as indicated above, in the form of the free base or converted to an acid-addition salt by reaction with an acid such as hydrochloric acid, sulfuric acid, phosphoric acid, pamoic acid, etc.

The compounds of the formula II can be prepared from novel intermediate compounds in a series of steps starting from the known material butirosin A. The preparation is described in detail in the examples set forth below. In this preparation, the amino groups of butirosin A are first each blocked with a protecting group, the tetra-N-protected butirosin A is converted to the 3',4',3'',5''-bis-O-cyclohexylidene derivative, the latter is acylated to form the tri-O-acyl derivative, and the latter is treated first with cold aqueous acetic acid to remove the 3',4'-cyclohexylidene group, then with trifluoromethanesulfonic anhydride and pyridine to yield a mixture of the 3'-O- and 4'-O-trifluoromethanesulfonyl compounds. The mixture is reacted with the sodium salt of an arylmercaptan and the resulting 3'-arylthio compound is purified and treated with warm aqueous acetic acid to remove the 3'',5''-cyclohexylidene group and then with ammonia or sodium methoxide to remove the three O-acyl groups, thereby yielding tetra-N-protected-3'-arylthio-3'-deoxybutirosin A (II).

The free base compound of the invention, as indicated, can be converted to an acid-addition salt; it forms such a salt with any of a variety of inorganic and organic acids. Pharmaceutically-acceptable acid-addition salts are formed with such acids as hydrochloric, hydrobromic, sulfuric, phosphoric, acetic, succinic, citric, maleic, malic, carbonic, gluconic, pamoic and related acids. The invention includes acid-addition salts generally as any salt which may be toxic can be converted to the free base or to a pharmaceutically-acceptable salt. The free base and the acid-addition salt forms are interconvertible by adjustment of the pH or by the use of ion-exchange resins. They differ in solubility properties, but except as noted above are otherwise equivalent for purposes of the invention.

In addition, the compounds of this invention and their acid-addition salts can exist in anhydrous forms as well as in solvated, including hydrated, forms. In general, the hydrated forms and the solvated forms with pharmaceutically-acceptable solvents are equivalent to the anhydrous or unsolvated form for the purposes of the invention.

The compounds of this invention and their acid-addition salts possess antibacterial activity. They show activity when tested by well-recognized in vitro antibacterial screening procedures. The following table shows typical results obtained from such procedures expressed in terms of the minimal concentration required to inhibit the growth of each of a number of representative bacterial species.

ACTIVITY TABLE

3'-Deoxybutirosin Carbonate: Antibacterial Activity in Vitro Compared with Butirosin and Gentamicin

| | Minimal Inhibitory Conc. by Microtitration in TSB[a] | | |
|---|---|---|---|
| Organism | Butirosin Sulfate | Gentamicin Sulfate | 3'-Deoxybutirosin A Dicarbonate |
| *Strep. faecalis* MGH-2 | >200 | 100 | >200 |
| *Staph. aureus* S18713 | 50 | 3.1 | 6.3 |
| *Klebs. pneumoniae* MGH-1 | 12.5 | 3.1 | 6.3 |
| *Serr. marcescens* IMM-5 | 12.5 | 3.1 | 12.5 |
| *Entero. eloacae* IMM-50 | 6.3 | 3.1 | 3.1 |
| *Pseud. aeruginosa* #28 | 12.5 | 3.1 | 3.1 |
| " VAD 12-7-7 | 25 | 6.3 | 6.3 |
| " 74C-1 | 25 | 6.3 | 6.3 |
| " 733 | 12.5 | 6.3 | 12.5 |
| " LA 3399 | 50 | 25 | 25 |
| " UI-18 | 25 | 6.3 | 6.3 |
| " Aquilar[b] | >200 | 50 | 25 |
| " G 76[c] | 50 | 100 | 12.5 |
| " PST-1[d] | 50 | >200 | 12.5 |
| " 58.3[§] | 25 | 6.3 | 25 |
| " 130[d] | 25 | 100 | 12.5 |
| *Esch. coli* JR 76.2[d] | >200 | 100 | 3.1 |
| " CW[d] | 6.3 | 100 | 3.1 |
| Providence 164 | >200 | 100 | >200 |

[a] Trypticase soy broth, standard procedure, overnight 37° C. incubation, approximately 100 viable units in inoculum.
[b] Butirosin and Gentamicin-resistant clinical isolates.
[c] Gentamicin-resistant clinical isolate.
[d] Produce aminoglycoside-antibiotic-inactivating enzymes.

Thus, the compounds of this invention and their acid-addition salts are of value for their antibacterial activity against a number of microorganisms and especially against *Pseudomonas aeruginosa* and certain butirosin and gentamicin-resistant microorganisms. They can be administered either parenterally or topically. They can also be used to sterilize the gastrointestinal tract by oral administration.

Because of their wide antibacterial spectrum, the compounds of the invention are also useful as antibacterial agents in in vitro applications such as sterilizing laboratory instruments and surfaces, sterilizing pharmaceutical products, and maintaining sterile conditions during pharmaceutical manufacturing operations. For sterilizing laboratory instruments and surfaces and similar in vitro applications, the compounds can be used in the form of a 0.1 to 1.0% aqueous solution.

The invention is illustrated by the following examples.

EXAMPLE 1

A stream of hydrogen was bubbled into a stirred solution of 687 mg. of 3'-deoxy-tetra-N-[(phenylmethoxy)carbonyl]-3'-(phenylthio)butirosin A in 14 ml. of methanol and 1.5 2N acetic acid. A slurry of 20% palladium oxide on barium sulfate (ca. 0.20 g.) in methanol, saturated with hydrogen, was added and hydrogenolysis was allowed to continue for 1.5–3 hrs. The process was repeated 20 times, during which enough methanol was added to maintain the volume of the reaction mixture, and a total of an additional 1.5 ml. of 2N acetic acid and 1.5 ml. water were also added. A total of 4263 mg. of catalyst and 51 hours of reaction time were employed to achieve complete hydrogenolysis of both the N-[(phenylmethoxy)carbonyl] and phenylthiol groupings.

The reaction mixture was filtered and the filter pad was washed with 70 ml. of methanol-1N acetic acid (1:1). The filtrate and washing were evaporated to a small volume in vacuo, with the temperature being kept below 25° C. Water was added, and evaporation was repeated. Finally water was added, and the solution was freeze-dried to give the acetate salt of 3'-deoxybutirosin A.

An aqueous solution of the acetate salt was adjusted to pH 6.3 with dilute ammonia and added to a column of 36 ml. of carboxymethyl dextran (CM-Sephadex C-25, medium ammonia form). The column was washed with 150 ml. of water, then with aqueous ammonia as a linear gradient from 0 to 0.25M during 30 min. The column was then developed with aqueous ammonia as a 4-hour linear gradient from 0.25 to 0.45M, followed by a 4-hour linear gradient from 0.45 to 1.0M, while 4-minute fractions (ca. 6 ml. each) were collected. The presence of the product in the eluate was detected by phenol-sulfuric acid test. Fractions 57–68 were combined and freeze-dried to give 3'-deoxybutirosin A in the free base form. The free base was dissolved in water, and the aqueous solution was saturated with carbon dioxide. The product, 3'-deoxybutirosin A, carbonate salt, was isolated by freeze-drying.

| Specific rotation (c 0.9%, water): | | | | |
|---|---|---|---|---|
| $\lambda$ | 589 | 578 | 546 | 436 | 365 |
| $[\alpha]$ | +15.4 | +15.6 | +17.6 | +28.6 | +41.4 |

EXAMPLE 2

3'-Deoxy-tetra-N-[(phenylmethoxy)carbonyl]-3'-(phenylthio)-butirosin A (0.90 g.) was dissolved with stirring in 40 ml. of dry liquid ammonia at −60° C. Anhydrous conditions were maintained throughout by the use of drying tubes. Freshly cut pieces of Na metal were added until the solution remained dark blue for 20–30 seconds. The blue color was removed by the addition of NH₄Cl and the ammonia gas evaporated. Residual ammonia was removed under vacuum and the white residue dissolved in 30 ml. of water. The pH was adjusted to 6.4 with 2N HCl and the solution extracted two times with 20-ml. portions of CHCl₃ to remove thiophenol. The resulting solution was then passed through a column (10 ml.) of carboxylic acid resin in the NH₄ cycle (such as Amberlite IRC-50) and washed with H₂O. Elution was accomplished with 1N NH₄OH followed by evaporation in vacuo and lyophilization. The product, 3'-deoxybutirosin A, was purified by re-chromatography on carboxymethyl dextran (CM-Sephadex) using linear gradient elution with aqueous ammonia from 0.2 to 0.8 normal. The purified product obtained was identical to that prepared by the method of Example 1.

STARTING MATERIALS

Tetra-N-[(phenylmethoxy)carbonyl]butirosin A

Methanol (350 ml.) was added to a solution of 25 g. of butirosin A base in 75 ml. of water. 25 G. of sodium bicarbonate was also added. The mixture was stirred and cooled to 5° C., and 25 ml. of (phenylmethoxy)carbonyl chloride (95%) was added dropwise during 20 minutes. An additional 10 g. of sodium bicarbonate was added and the mixture was stirred at 5° C. for 1 hour. The reaction mixture was further treated with 10 g. of sodium bicarbonate and 10 ml. of (phenylmethoxy)carbonyl chloride, which was added dropwise, stirred for 3 hours at 0° and 2 hours at room temperature, then allowed to stand overnight at ca. 3° C. The liquid phase was decanted from the solid and evaporated in vacuo to a small volume so that most of the water was removed. The residual solid was extracted two times with 50-ml. portions of water, dissolved two times in 200 ml. of absolute ethanol, each time being followed by evaporation of the ethanol to dryness in vacuo. The residue was again dissolved in 200 ml. of ethanol; the solution was filtered, evaporated to dryness in vacuo and triturated with ether to give tetra-N-[(phenylmethoxy)carbonyl]-butirosin A (Rf 0.41 in a solvent mixture made of 10 ml. of methanol diluted to 100 ml. with chloroform, i.e., 10% methanol in chloroform; Rf values herein were from thin-layer chromatography using silica gel plates, Quanta Q1F, 10 cm. length).

3',4',3'',5''-Bis-O-Cyclohexylidene-tetra-N-[phenylmethoxy)carbonyl]butirosin A 1.313 G. of p-toluenesulfonic acid monohydrate and 10.0 ml. of dimethoxycyclohexane were added to a solution of 10.00 g. of tetra-N-[-(phenylmethoxy)carbonyl]butirosin A in 100 ml. of dried N,N-dimethylformamide in a 300 ml. 3-necked flask. The flask was fitted with a coil condenser, the top of which was connected through a stopcock to a vacuum of 13–14 mm. mercury. The flask was also fitted with a fine capillary through which air previously dried with concentrated sulfuric acid was allowed to bubble into the solution in vacuo. With the solution in vacuo, the flask was placed in a water bath for 50.5° C. for 32 minutes. The flask was then removed from the water bath, cooled with water at room temperature, and the stopcock was closed. After 25 minutes, the stopcock was opened allowing the introduction of dried air, and 3 ml. of triethyhlamine was added with swirling. The solution was evaporated in vacuo (bath temperature 45° C. or below) to give the product, 3',4',3'',5''-bis-O-cyclohexylidene-tetra-N-[(phenylmethoxy)carbonyl]butirosin A.

For purification, the product in 50 ml. of chloroform was added to a column of 200 g. of silica gel packed in chloroform (2.8 cm. × 86 cm.). The column was developed with 450 ml. of chloroform, 1610 ml. of 3% methanol in chloroform, and 200 ml. of 4% methanol in chloroform. The final 800 ml. of the eluate was collected in small fractions. Various small fractions were combined and evaporated to give three main fractions of the product as dry solid.

Tri-O-acetyl-3',4',3",5"-bis-O-Cyclohexylidene-tetra-N-[(phenylmethoxy)carbonyl]butirosin A 2.9 Ml. of acetic anhydride was added to a solution of 2.163 g. of 3',4',3",5"-bis-O-cyclohexylidene-tetra-N-[(phenylmethoxy)carbonyl]butirosin A in 12.5 ml. of dried pyridine. After 2 days at room temperature the solution was evaporated to a syrup in vacuo, then co-evaporated with 30 ml. of p-xylene and dried in vacuo overnight to give the product tri-O-acetyl-3',4',3",5"-bis-O-cyclohexylidene-tetra-N-[(phenylmethoxy)carbonyl]butirosin A (Rf 0.51, 2% methanol in chloroform).

2",2''',6-Tri-O-acetyl-3",5"-O-cyclohexylidene-tetra-N-[(phenylmethoxy)carbonyl]butirosin A 9.7 Ml. of water was added dropwise, with swirling, to a solution of 1.866 g. of tri-O-acetyl-3',4',3",5"-bis-O-cyclohexylidene-tetra-N-[(phenylmethoxy)carbonyl]-butirosin A in 17.6 ml. glacial acetic acid. After 2 hours at room temperature, the reaction was evaporated to a syrup in vacuo, then co-evaporated in vacuo with chloroform and 20 ml. of xylene, and further dried in vacuo to provide 2",2''',6-tri-O-acetyl-3",5"-O-cyclohexylidene-tetra-N-[(phenylmethoxy)carbonyl]butirosin A.

The product, together with the yield from two other runs (5.80 g.), in 15 ml. of chloroform, was added to a column of 50 g. of silica gel packed in chloroform (2.4 cm. × 28.7 cm.). The column was developed, in succession, with 15 ml. of chloroform, 100 ml. of 1% methanol in chloroform and 485 ml. of 2% methanol in chloroform. The product on evaporation was obtained in pure form from the last 325 ml. of the eluate (Rf., 0.20, 2% methanol in chloroform).

2",2''',6-Tri-O-acetyl-3",5"-O-cyclohexylidene-tetra-N-[(phenylmethoxy)carbonyl]-3'-O-[(trifluoromethyl)sulfonyl]butirosin A A solution of 2.56 ml. of trifluoromethanesulfonic anhydride in 33 ml. of dried methylene chloride was added dropwise, during 25 minutes, to a stirred solution of 4.445 g. of 2",2''',6-tri-O-acetyl-3",5"-O-cyclohexylidene-tetra-N-[(phenylmethoxy)carbonyl]butirosin A in 50 ml. of dried methylene chloride and 16 ml. of dried pyridine, kept at −10° C. After 70 minutes at −10° C., 15 ml. of water was added dropwise and the mixture was stirred vigorously for about 10 minutes with the ice bath removed. The reaction mixture was then shaken, in succession, with 42.5 ml. of 4N hydrochloric acid, 16 ml. of 0.25N hydrochloric acid, 15 ml. of water, 27 ml. of 8% sodium bicarbonate, then three times with 15-ml. portions of water. A total of 21 ml. of methylene chloride was also added at various stages of the extraction. The extracted product was dried over sodium sulfate and concentrated to dryness by evaporation to provide the product 2",2''',6-tri-O-acetyl-3",5"-O-cyclohexylidene-tetra-N-[(phenylmethoxy)carbonyl]-3'-O-[(trifluoromethyl)sulfonyl]butirosin A.

2",2''',6-Tri-O-acetyl-3",5"-O-cyclohexylidene-3'-deoxy-tetra-N-[(phenylmethoxy)carbonyl]-3'-(phenylthio)butirosin A 5.5 Ml. of benzenethiol was added dropwise during 40 minutes to a stirred suspension of 1.690 g. of sodium hydride (50% in mineral oil) in 10.0 ml. of dried N,N-dimethylformamide, cooled over an ice bath. The solution was cooled to −6° C. and added to a solution of 4.642 g. of 2",2''',6-tri-O-acetyl-3",5"-O-cyclohexylidene-tetra-N-[(phenylmethoxy)carbonyl]-3'-O-[(trifluoromethyl)sulfonyl]butirosin A in 7.0 ml. of dried N,N-dimethylformamide, which had been prepared at 0° C. and cooled to −6° C. The mixture was stirred for 16 hours at −6° C. to −2° C. After an additional 4 hours at −6.5° C. and 5 hours at −10° C., a solution of 4.7 ml. glacial acetic acid in 13 ml. of ether was added with stirring to convert the excess benzenethiolate ion to benzenethiol. The mixture was evaporated in vacuo, using a bath temperature of 25° C. during most of the evaporation, then 35° C. for 20 minutes, 40° C. for 10 minutes, 45° C. for 5 minutes, and finally room temperature for 2 hours, yielding the product 2",2''',6-tri-O-acetyl-3",5"-O-cyclohexylidene-3'-deoxy-tetra-N-[(phenylmethoxy)carbonyl]-3'-(phenylthio)butirosin A, as a residue. A solution of the product in 250 ml. of chloroform was washed with 20-, 15-, 15- and 10-ml. portions of water, dried with anhydrous sodium sulfate, and evaporated in vacuo. The dry product was kept in vacuo at 45° C. for 5 minutes and overnight at room temperature.

A solution of the product in 7.5 ml. of chloroform and 7.5 ml. of benzene was chromatographed over a column containing 60 g. of silica gel. The column was developed with 100 ml. of chloroform, 100 ml. of 0.75% methanol in chloroform, and 200 ml. of 1.5% methanol in chloroform. The column was then developed with 185 ml. of 1.5% methanol in chloroform while 5-min. fractions (fr. 5 to 26) and then 10-min. fractions (fr. 27 to 38) were collected. The column was then developed with 105 ml. of 2% methanol in chloroform while fractions 38 to 66 were collected. Fractions 14 through 39 containing the product 2",2''',6-tri-O-acetyl-3",5"-O'cyclohexylidene-3'-deoxy-tetra-N-[(phenylmethoxy)carbonyl]-3'-(phenylthio)butirosin A (Rf. ca. 0.53, 2.5% methanol in chloroform) were combined and the product in pure form was isolated by evaporation of the solvent.

2",2''',6-Tri-O-acetyl-3'-deoxy-tetra-N-[(phenylmethoxy)carbonyl]-3'-(phenylthio)butirosin A 14.1 Ml. of water was added dropwise with swirling to a solution of 1.142 g. of 2",2''',6-tri-O-acetyl-3",5"-O-cyclohexylidene-3'-deoxy-tetra-N-[(phenoxymethoxy)carbonyl]-3'-(phenylthio)-butirosin A in 25 ml. of glacial acetic acid. The solution was kept at 45° C. for 19.5 hours. The solution was evaporated in vacuo to provide the product, 2",2''',6-tri-O-acetyl-3'-deoxy-tetra-N-[(phenylmethoxy)carbonyl]-3'-(phenylthio)butirosin A (Rf. 0.21 in 2.5% methanol in chloroform).

3'-Deoxy-tetra-N-[(phenylmethoxy)carbonyl]-3'-(phenylthio)butirosin A (a) Methanolic ammonia method.

A solution of 1.074 g. of 2",2''',6-tri-O-acetyl-3'-deoxy-tetra-N-[(phenylmethoxy)carbonyl]-3'-(phenylthio)butirosin A in 70 ml. of absolute methanol, saturated with anhydrous ammonia at 0° C., was allowed to stand at the same temperature for 21 hours. The solution was evaporated to dryness in vacuo, dissolved in 5 ml. of chloroform and added to a column containing 13.0 g. of silica gel in chloroform (1.2 cm. × 37.0 cm.). The column was developed with 23 ml. CHCl₃, 20 ml. 1% methanol in chloroform, 25 ml. of 2.5% methanol in chloroform, and 34 ml. of 5% methanol in chloroform. The column was then developed with 100 ml. of 8% methanol in chloroform while 4-min. fractions (1 to 35) were collected. Fractions 11–15 were combined. Fractions 9, 10, and 16–25 were separately purified further on 20 cm. × 20 cm. preparative thin layer chromatography plates. The product from each of fractions 9, 10, 11–15 and 16–25 was 3'-deoxy-tetra-N-[(phenylmethoxy)carbonyl]-3'-(phenylthio)butirosin A.

(b) Sodium methoxide method.

1.3 G. of 2'',2''',6-tri-O-acetyl-3'-deoxy-tetra-N-[(phenylmethoxy)carbonyl]-3'-(phenylthio)butirosin A in 40 ml. of dry MeOH was cooled to 5° C., and 50 mg of NaOCH₃ was added with stirring. The mixture was allowed to stand at 5° C. overnight and then neutralized by the addition of 1 ml. of aqueous 2N acetic acid. The mixture was evaporated to dryness in vacuo and triturated with ice water. Filtration and drying in vacuo afforded the product 3'-deoxy-tetra-N-[(phenylmethoxy)carbonyl]-3'-(phenylthio)butirosin A.

We claim:

1. Process for the production of 3'-deoxybutirosin which comprises reducing a compound of the formula

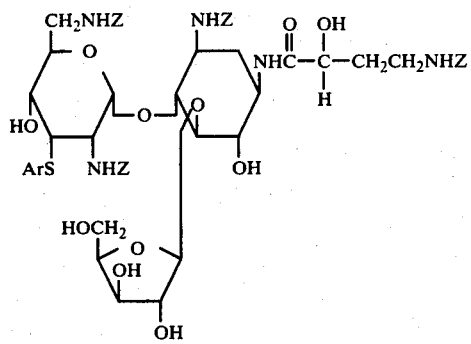

with a reducing agent which is molecular hydrogen in the presence of a noble metal catalyst or sodium in liquid ammonia, wherein Z is a protective group of the formula

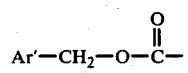

and each of Ar and Ar' is an aryl group having one of the formulas

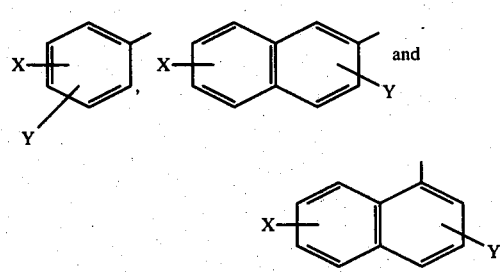

wherein each of X and Y is hydrogen, halogen, nitro, lower alkyl of from one to four carbon atoms, or lower alkoxy of from one to four carbon atoms.

2. The process of claim 1 wherein Z is carbobenzoxy and Ar is phenyl.

* * * * *